United States Patent [19]
Nevel et al.

[11] Patent Number: 6,130,746
[45] Date of Patent: Oct. 10, 2000

[54] SYSTEM AND METHOD FOR ELECTRONICALLY EVALUATING PREDICTED FABRIC QUALITIES

[75] Inventors: Avishai Nevel, Providence; Kendall W. Gordon, Jr., North Kingston, both of R.I.; David Bonneau, West Boylston, Mass.

[73] Assignee: Lawson-Hemphill, Inc., Central Falls, R.I.

[21] Appl. No.: 08/603,587

[22] Filed: Feb. 21, 1996

Related U.S. Application Data

[63] Continuation-in-part of application No. 08/252,346, Jun. 1, 1994, Pat. No. 5,570,188, and a continuation-in-part of application No. 08/209,421, Mar. 10, 1994, Pat. No. 5,514,734.

[51] Int. Cl.[7] .................................................. G01N 21/89
[52] U.S. Cl. .............................. 356/238.2; 250/559.24; 356/430; 83/361; 83/371; 28/227
[58] Field of Search .................................... 356/385, 384, 356/386, 387, 429, 430, 431, 238, 238.2; 250/559.24; 364/578; 28/227; 83/361, 371

[56] References Cited

U.S. PATENT DOCUMENTS

| 4,078,253 | 3/1978 | Kajiura et al. ............................ 364/900 |
|---|---|---|
| 4,152,767 | 5/1979 | Laliotis . |
| 4,169,399 | 10/1979 | Glockner et al. .......................... 83/361 |
| 4,184,769 | 1/1980 | Aeppli ...................................... 356/430 |
| 4,189,841 | 2/1980 | Loepfe ....................................... 33/147 |
| 4,430,720 | 2/1984 | Aemmer .................................... 364/552 |
| 4,465,937 | 8/1984 | Forbes ....................................... 250/560 |
| 4,481,820 | 11/1984 | Thomann .................................... 73/597 |
| 4,491,831 | 1/1985 | Sakai et al. ............................... 340/677 |
| 4,537,202 | 8/1985 | Mancini et al. ........................... 128/712 |
| 4,585,947 | 4/1986 | Liptay-wagner et al. . |
| 4,648,054 | 3/1987 | Farah et al. ............................... 364/552 |
| 4,656,465 | 4/1987 | Erni et al. ................................. 340/679 |
| 4,719,060 | 1/1988 | Ragone ..................................... 264/412 |
| 4,753,532 | 6/1988 | Alfred . |
| 4,758,968 | 7/1988 | Lord ......................................... 364/552 |

(List continued on next page.)

FOREIGN PATENT DOCUMENTS

| 1258530 | 8/1989 | Canada . |
|---|---|---|
| 0578975A1 | 1/1994 | European Pat. Off. . |
| 3230754A1 | 3/1983 | Germany . |
| 3303770C1 | 12/1983 | Germany . |
| 58-180911A | 10/1983 | Japan . |
| 1327242 | 8/1973 | United Kingdom . |
| 1421911 | 1/1976 | United Kingdom . |
| 2236387 | 3/1991 | United Kingdom . |

OTHER PUBLICATIONS

Jeong and Suh, Prediction of Yarn and Fabric Qualities Based on Uster Signal Processing, Nov. 1993.

Jeong and Suh, Visualization of Fabric Qualities Through Signal Processing of Yarn Profiles, Nov. 1994.

Sung and Jeong, Statistical Modeling of Spun Yarn Characteristics Under HVI Data Environment, Oct. 1994.

Keisokki Report, Oct. 1983.

Stein, Rechnergesteuerte Zugprufgerate, Textil Praxis International 1984, Jan.

Keisokki Report, Sep. 1985.

Marwinski, et al., Non–destructive testing of twist for large packages of cabled technical yarns, Chemizfasern/Textilindustrie, vol. 43/95, Jun. 1993.

*Primary Examiner*—F. L. Evans
*Attorney, Agent, or Firm*—Nields, Lemack & Dingman; Brian M. Dingman

[57] ABSTRACT

A system or method for electronically simulating fabrics to assist in grading yarn and fabric qualities, in which the diameter or other qualities of one or more yarn samples along the total length of the samples is measured, and representations of the measured yarn qualities are evaluated in a fabric pattern to assist evaluation of the effects of the yarn quality variations on fabric which potentially would be produced from the sampled yarn.

2 Claims, 12 Drawing Sheets

U.S. PATENT DOCUMENTS

| | | | |
|---|---|---|---|
| 4,764,876 | 6/1993 | Whitener, Jr. et al. | |
| 4,812,043 | 3/1989 | Vanstaen | 356/385 |
| 4,885,709 | 12/1989 | Edgar et al. | |
| 4,887,155 | 12/1989 | Massen | 348/88 |
| 4,954,976 | 9/1990 | Noonan | 364/578 |
| 4,963,757 | 10/1990 | Liefde et al. | |
| 4,984,181 | 1/1991 | Kliman et al. | 395/129 |
| 5,016,183 | 5/1991 | Shyong | 364/470.02 |
| 5,088,827 | 2/1992 | Kyriakis | |
| 5,146,550 | 9/1992 | Furter et al. | 395/140 |
| 5,181,374 | 1/1993 | Aeppli | 57/264 |
| 5,537,811 | 7/1996 | Pidous et al. | |
| 5,671,061 | 9/1997 | Hoeller | 356/429 |

SYSTEM AND METHOD FOR ELECTRONICALLY EVALUATING PREDICTED FABRIC QUALITIES

RELATED APPLICATIONS

This application is a continuation-in-part of applications Ser. No. 08/252,346, filed Jun. 1, 1994, now U.S. Pat. No. 5,570,188, and Ser. No. 08/209,421, filed Mar. 10, 1994, now U.S. Pat. No. 5,514,734.

FIELD OF THE INVENTION

This invention relates to a system and method for rapidly and electronically scanning long lengths of one or more yarns, and displaying measured qualities of a large number of selected lengths of the yarn in a fabric pattern to assist in the evaluation of the effects of the quality variations on the quality of fabric which potentially would be produced from the one or more yarns.

BACKGROUND OF THE INVENTION

There are numerous quality tests for yarns and the fabric they will produce. One such test is for the general appearance of the fabric. This test is accomplished by weaving or knitting the subject yarns into a fabric sample. Yarn quality defects and effects, such as color inconsistencies, width inconsistencies, hairiness, slubs, broken ends, and other novelty effects can thereby be judged as they will affect fabric quality, unarguably the most critical aspect of the yarn. The occurrence of yarn defects in close proximity on the fabric, of undesirable defect patterns, of a multitude of marginally acceptable yarn defects creating an unacceptable fabric defect, can be visually observed and quantified. This test has been standardized as ASTM D2255/90 and ASTM D2255. It has become the accepted method for predicting the quality of fabric to be produced from entire lots of sampled yarns based on the probability that unacceptable fabric defects will be observed in a sample of this size.

Fabric quality will be affected by other factors as well as yarn quality, such as loom defects. Because looms and knitting machines intended for high production runs of fabric cannot practically be interrupted for the running of small test runs, as reasoned below, the machines used for test sample runs tend to be smaller, older, worn, or obsolete models whose results would be generally unacceptable for producing marketable fabric. Variations in tension on one or more yarn strands during weaving or knitting will cause fabric variations that might be read as resulting from poor yarn quality. Sinusoidally occurring loom inconsistencies will cause recurring fabric faults whose regularity may not be recognized in the small test sample, and may therefore be read as resulting from poor yarn quality. Other loom deficiencies and also ambient temperature and humidity conditions may affect fabric quality independently of the quality of the yarn from which it was produced. Obviously, the grading of yarn in fabric samples is a somewhat qualitative process, leaving the possibility that one grader might judge a sample quite differently than another grader, that the subject sample might not accurately represent the fabric to be produced, or that defects will be missed as a result of the small sample size.

Other drawbacks to the current grading system are that it requires the actual weaving or knitting of a fabric sample, or winding the yarn on a board, which requires specialized equipment and specialized operator training, or an actual loom or knitting machine. Test samples can be produced using an instrument such as a Fiber Analysis Knitter (FAK) like that manufactured by Lawson-Hemphill, Inc., of Central Falls, R.I. Looms and knitting machines are huge and complicated machines requiring many manual settings and adjustments independent to each run. These machines cannot practically fit within small quality labs and require operator expertise not typical of lab personnel. A significant amount of the time taken to produce a fabric run is in the set-up of the machine. Each fabric pattern requires a different loom set-up procedure. Looms are quite expensive to purchase and operate, take up substantial floor space, and must be used efficiently in the production of marketable fabric in order to justify their high cost. For reasons of time and cost, the practice of setting-up a production loom to run a few small test samples of a particular fabric would be impractical. Test samples are generally run on smaller weaving or knitting machines which are more practical for this application even though those tend to be slow and to have outputs which may not be fully indicative of production fabric.

Further drawbacks to the current test sample making method is that many actual yarn sample spools are required to run even these small test samples, and the yarn waste percentage is very high on such a short run.

It can readily be seen that the current fabric grading method is very slow, inaccurate, labor intensive, highly judgmental and expensive.

SUMMARY OF THE INVENTION

It is therefore the object of this invention to provide a system and method for electronically displaying simulated fabric including one or more measured qualities of a large number of yarn lengths, measured from one or more yarn samples, to assist in predicting fabric quality as it would be affected by those measured yarn qualities.

The term "display" as used herein is meant to encompass human-viewable computer outputs, such as a CRT or a printer output, and/or a machine-interpretable data set-such as the data from which a visible display could be derived, depending on the possibilities in each given use. As explained herein, the data set is created from measurements, or representations of such measurements, taken along one or more lengths of yarn.

This invention results from the realization that a fabric sample evaluation test may be accomplished electronically by scanning long lengths of one or more yarn samples from one or more yarn cones and arranging and displaying the long lengths of yarn as a number of interwoven shorter lengths in a typical fabric pattern to electronically simulate the manual fabric test sample currently in use, and by representing different measured yarn qualities with display attributes such as their actual image, display line width or length, shades of grey, colors, or numerical or other values, to allow the visual evaluation of the simulated fabric as done manually with fabric samples, and also allow electronic yarn gradings and actual counts of faults or events in the yarn and fabric.

It is a further object of this invention to provide such a system and method that is less expensive to accomplish than the manual system. The need for valuable loom time is virtually eliminated. Fabric simulations will most often be sufficient to judge yarn lot acceptability.

It is a further object of this invention to provide a system for predicting the quality of finished goods made of fabric woven or knitted from a particular yarn sample.

It is a further object of this invention to provide such a system and method that is quicker than the manual system.

Yarn measurements can be converted to simulated fabric almost instantly. Loom set-up time and run time is eliminated.

It is a further object of this invention to provide such a system and method that is easier and less labor intensive than the manual system. Once a yarn length is measured, manual labor to provide the simulated fabric display can be reduced to a few keystrokes.

It is a further object of this invention to provide such a system and method that provides results which can be more accurately quantified, and thereby eliminate human judgement. The number of yarn faults on a fabric sample can be readily established. The proximity of yarn faults/qualities, and their relationship within a predetermined fabric zone can be evaluated and quantified or stored. These results can then be compared to an established tolerance or reference to eliminate the subjectivity of the current grading process. One or more simulated fabric images could be displayed simultaneously on a CRT screen to compare one simulated fabric to another, or to a standard. One yarn could be displayed simultaneously woven into one or more patterns, or woven with other yarns.

It is a further object of this invention to provide such a system and method that allows for the grading of a greater quantity of yarn cones and fabric test samples than is currently accomplished. Any possible arrangement of any number of woven or knitted yarns can be accomplished rapidly. Worst-case scenarios can be located and the statistical probability of their occurrence can be instantly calculated.

It is a further object of this invention to allow rapid and inexpensive evaluation of yarn in many known fabric patterns. A single yarn sample may be measured and its representation may be electronically "knitted" into a particular knit pattern, or that representation may serve as both the weft and warp yarns in a particular weave pattern. One yarn samples' representation may be used continuously as the weft of a simulated woven fabric patch, while a multitude of other yarn sample's representations are used as the warp yarns in the same pattern. From one or a few small samples of yarn, a large number of fabric patterns may be evaluated, saving time, labor, and cost.

It is a further object of this invention to eliminate the waste associated with the current ASTM test sample system, and to simplify inventory control. Fabric samples being simulated instead of actually produced require only those yarn samples being measured. No yarn is wasted at the loom. Once measured, the data file for a given sample can be used repeatedly. Yarn lengths can be instantly "woven" with other measured yarns in any known pattern to find an acceptable match for otherwise unacceptable lots of yarn. Yarn lots can be "fingerprinted" with their measurement data and filed electronically. Then, when a fabric grade requirement necessitates that yarn within certain qualities be selected, yarn lot fingerprint files can be searched electronically to locate from inventory acceptable yarn lots, and instantly provide displays of simulated weavings. Yarn lots can be quantitatively graded according to their effect on fabric quality, or on fabric quality for certain patterns. A yarn lot could be graded A for one given weave pattern, and B for another pattern, based solely on the results of simulated weave analysis, with no actual weaving having been done. The invention can thereby serve to determine the best application for a given yarn. A yarn with certain fault characteristics may be unacceptable for one use, but perfectly acceptable for another use. The system could thereby help to determine the most appropriate use for a particular yarn sample, reducing rejection and waste. The system can be adapted for on-line measurement of yarn under production (this is very important), allowing for tagging of a yarn run with it's fingerprint data as it is produced, simplifying inventory control and eliminating the need for post-production measurement.

Yarn lengths can be imaged with a video camera, and the data stored as computer files which can be manipulated to enhance or to filter out selected qualities. Then the files can be interwoven to provide a realistic image of the resulting fabric. Images can be distorted electronically to imitate the twists and bends of actual weaving or knitting. Image portions can be deleted to imitate passage behind other images. The image could be displayed in three dimensional fashion so that the effects of twists and non-linearities on the yarns in the fabric, and the effect on the fabric as a whole by such non-linearities, can be displayed.

Results from the simulated fabric evaluation can be used to correct production faults. Corrections can be electronically simulated as well to determine their effects in improving defective yarn. Video color adjustments could be made, for instance, to instantly determine the results of die color changes on the final fabric.

Feedback from the electronic system can be used not only as an end-product evaluation tool, but also as an in-process correction tool. When adapted for on-line measurement, weaves can be instantly simulated and quantified, with or without a display, and the results fed instantly back to the appropriate production equipment to correct yarn production and reduce rejection rates. Yarn production will become more efficient and thereby faster.

This invention contemplates measurement of any measurable yarn quality, and use of such measurements for the stated objectives. Such measurable qualities include (but are not limited to), diameter and its average, coefficient of variation and standard deviation, evenness, hairiness, the ratio of core-to-hair thickness, twist, color, neps, and thick and thin areas.

The described concepts of yarn quality measurement and representation determination can be used to automatically, by use of a computer, "grade" the yarn itself, or an electronically-created "fabric". This would not require a visible display or printout. Such grading can be accomplished by programming the computer so that types, locations, and sizes of faults (called "events") that result in a particular grade are known. The computer could include a neural network programmed to weight events properly, and combine weightings properly, to simulate human judgment used in manual grading. The neural network would originally be input with information from expert human inspectors regarding the relative importance of each particular event, and of patterns of events, in determining yarn/fabric grade.

Types, quantity, location and patterns of events all contribute to quality determination. Patterns can be determined by electronically "dividing" the display into display areas or cells that are portions of the whole, or possibly the entire, data set. Quantities of event(s) in the cells can be counted, and evaluated cell-by-cell if desired. Unacceptable event patterns could be determined based on a concept as simple as any cell with a given percentage more than the average cell event quantity for any one or more particular events, or by more complex cell comparisons. A simple example of this concept could be that if a certain event occurs in any two vertically or horizontally adjacent cells, there is an unacceptable pattern.

This invention can be utilized to simulate the effect of a traditional yarn clearer on the measured yarn, and also to dynamically instruct a downstream yarn clearing device to remove certain measured events to upgrade the measured yarn. The first goal can be accomplished by electronically deleting certain measured events, and potentially evaluating the difference in yarn or fabric grade accomplished by such electronic clearing. The second goal can be accomplished by making the necessary measurements upstream of a yarn clearing device, and electronically determining the measured event(s) that needed to be cleared to create a desired yarn/fabric grade.

For Dynamic Yarn Clearing (DYC), a reservoir of a sufficient length of yarn between the measurement point and the clearer could be used to both provide the necessary time delay after measurement for the system to make the necessary calculations, and also to allow the comparison of multiple events occurring over the reservoir length of yarn as it would affect the grade. For example, a particular event could be acceptable if it occurred no more than once every two hundred meters. A two hundred meter reservoir could be used, and if two such events were measured over this length, only one would be cleared. This system would save time and cost over traditional clearing, in which the clearer is set to remove each and every fault of a certain width and length. In the case above, such a traditional clearer would remove both events, when only one needed to be removed for the desired grade, or for the intended yarn use. The dynamic yarn clearing of this invention thus measures one or more measurable yarn qualities, as well as the length of yarn measured, and makes clearing decisions based on both.

BRIEF DESCRIPTION OF THE DRAWINGS

Other objects, features, and advantages will occur to those skilled in the art from the following description of the preferred embodiments and the accompanying drawings in which.

DESCRIPTION OF THE PREFERRED EMBODIMENTS

This invention may be accomplished in a system for electronically measuring yarn portions, then electronically assembling those measured yarn portions, or representations of the measured yarn portions, into a simulated fabric patch to assist in determining yarn and fabric quality. The system may be adapted to simulate woven and/or knitted fabrics. The system preferably determines the yarn diameter at a large number of closely spaced locations along a length of yarn. This may be accomplished with an electronic sensor which may include a linear CCD array and a light source for shining a light into a measurement zone through which the yarn is moved. The CCD captures a shadow image of the yarn. The system then determines from this shadow image the yarn diameter. The diameter in one embodiment is based on the farthest-spaced pair of the CCD pixels LAWS/9415/US 13 that do not receive light, so that the yarn diameter measurement includes measurement of hairs, slubs and other thick spots in the yarn. Alternatively, diameter can be measured in more traditional manners, for example by summing the closed or blocked pixels of the CCD array. Such an imaging system can also be used to determine yarn color in order to determine the dyeability of the measured yarn.

The system is further capable of effectively deleting any hairiness which may extend from the yarn core or body, to allow the display observer to look at only the core itself. This may be accomplished by setting a desired light intensity threshold at the CCD so that thin hairs, which only attenuate and do not block the light, are not detected. This is essentially a hairiness threshold. This is of particular value because much of the hairiness of yarn is removed or obscured in the processes which turn the yarn into finished products such as clothing. The system is thereby uniquely capable of providing a prediction of the quality of finished goods made of fabric woven or knitted from the particular yarn sample.

These yarn diameter measurements are then electronically compared to predetermined length and width values. Instances where the diameter of the yarn exceeds or is less than (by some set amount) a preset width over at least, or less than, a preset length, are determined and recorded as "events". Alternatively, other yarn qualities, or quality variations, may be similarly measured and recorded as events. Display representations of the events in the measured yarn sample or samples are then divided into a number of groups of measurements representing adjacent, or closely spaced, shorter lengths of yarn. These may then be arranged side-by-side in a human-visible display to imitate the yarn layout in a rectangular or taper board as used in current manual yarn inspection tests, or they may be arranged in any of a number of standard weave or knit patterns to mimic a standard fabric test patch. The pattern may be a typical weave pattern such as a Plain, Twill, or Satin weave, having an interlaced array of horizontal and vertical representations.

The representations are typically linear series of line segments, the segments having lengths equal to the measured event lengths. The segment widths may be directly related to the measured diameter of the event so that the overall appearance of the representation is similar to that of a black yarn, in which case the yarn diameter may be represented by the width of the black line. Alternatively, the line segments could be of constant width and the yarn diameter, if represented at all, may be represented using grey scale or color. The pattern may also be a typical single jersey knit pattern such as a Tricot, Raschel, or LaCoste knit, wherein the yarn representations are looped in interconnected chains or rows all arranged in a basically horizontal or vertical direction.

In one embodiment, each point or value in the string of event representation data may be converted to a string of 8-bit images, and each pixel may have a value of between 0 and 255 to accomplish a grey-scale representation of event width. Alternatively, different event value ranges may be represented by different shades of grey or colors as desired to accomplish a system that facilitates the determination of overall yarn quality by the operator.

The relationship of events within proximity to one another on the simulated wound board or fabric may be evaluated electronically and assigned values. These values may also then be represented by numerical quantities or by various shades of grey or color as desired to accomplish a system that allows the computer and/or the operator to judge fabric quality as it is affected by the types, quantity, proximity and relationship of yarn events. The operator may select only instances where the summary of events of a particular yarn imperfection within a given fabric zone exceed a predetermined threshold, or where a threshold number of such events within a given zone is exceeded.

The system may be programmed to evaluate the statistical probability of an occurrence of any number of yarn quality variations such as fabric color blotches or thin fabric areas caused by the possible grouping of such events.

The system may be programmed to include common loom induced fabric defects to evaluate the potential fabric quality effects caused by the combination of such with the patterns of yarn events. Alternatively, the lengths of compared yarn portions and/or the display width may be varied to simulate the use of different loom widths. For example, if a yarn had a recurrent defect, an unacceptable fabric pattern might result if that yarn is woven on a loom with a width that is harmonically related to the spacing of the defect. The system can be adapted to display the yarn as it would be woven on looms of various widths, even displaying those simultaneously, to determine a loom on which the particular yarn could be used to acceptably intersperse the defects throughout a fabric. This could reduce waste while allowing lower quality yarn lots to be classified as higher quality for some applications.

Figure 1:
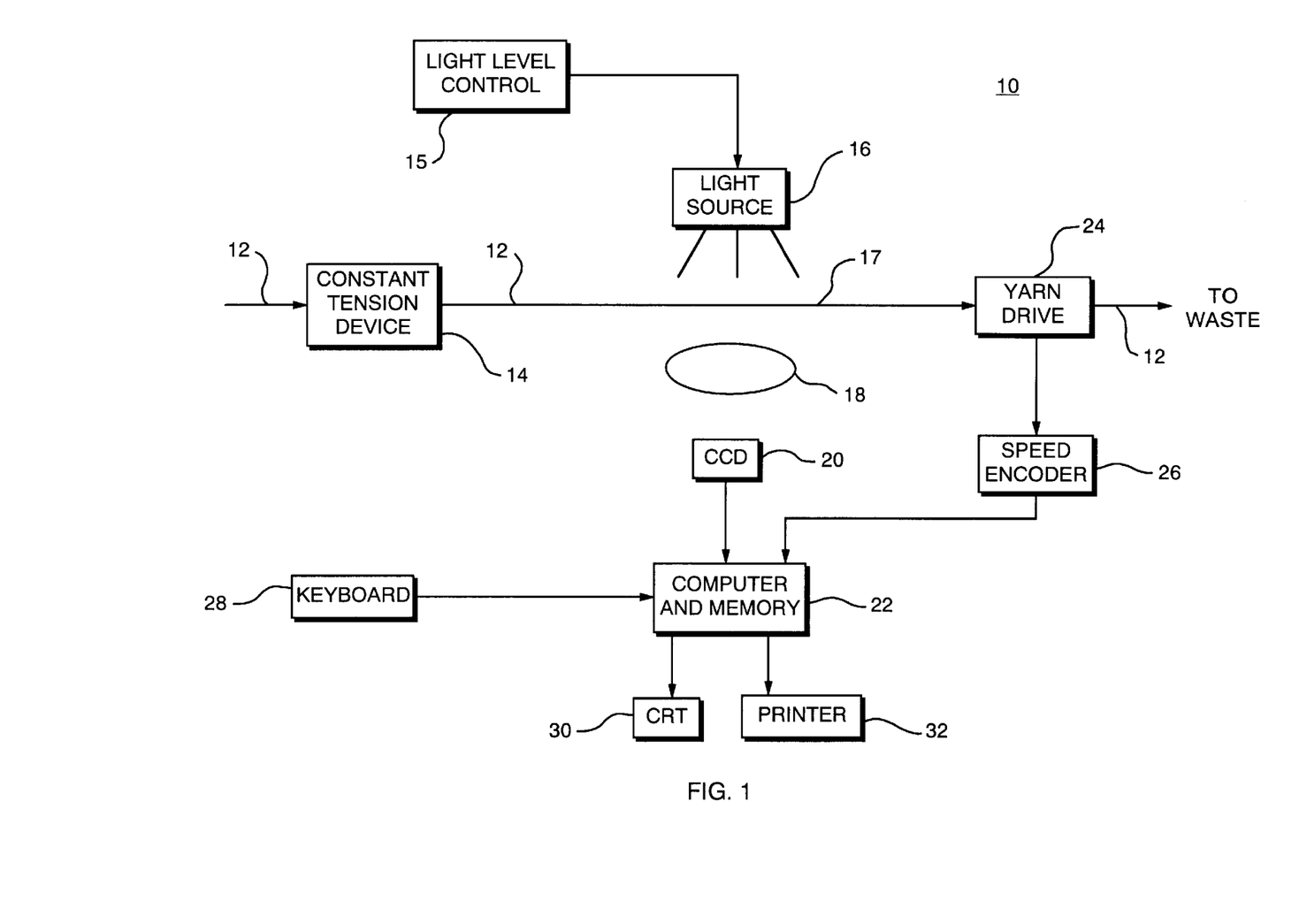
FIG. 1 is a schematic diagram of a yarn profile imaging/fabric simulating device useful in accomplishing this invention.

There is shown in FIG. 1 a yarn profile measurement and fabric quality determination and simulation system 10 useful in this invention. System 10 accomplishes the yarn diameter measurements and display in a fabric pattern to assist the operator in determining, or determine automatically itself, yarn and fabric quality. System 10 is used to make width measurements of yarn 12 moved through imaging area 17 by yarn drive 24. Yarn 12 may pass through constant tension device 14 before entering imaging area 17 so that it may be held under a constant, reproducible tension while being imaged. Precision control of the yarn speed is accomplished with yarn drive 24 so that the yarn may be passed through imaging area 17 at a constant, reproducible speed. This speed and tension control provides the ability of device 10 to develop useful, accurate, quantitative data concerning each unit of yarn under test.

Light source 16 provides light in imaging area 17 that is focused by lens 18 onto linear CCD array 20 to create an image sharp enough for the desired purposes. Light level control 15 allows operator control of the light output level of light source 16. Preferably, light source 16 is an incandescent lamp, and control 15 is a regulated DC lamp power supply with variable output to provide a steady light source without 60 Hz flicker that has a variable light-level output so that the operator may regulate the amount of light received by the CCD pixels that is considered to be a blocked pixel. The amount of light sensed by each pixel of array 20 is provided as a related analog voltage at the output of array 20.

This level can be compared to an adjustable, operator established threshold level in computer 22 so that the device reports a blocked (unlighted) pixel only when the selected percent of the maximum possible incident light actually received is below the selected threshold level. This threshold and light level flexibility allows the operator to either emphasize or filter out specific details of a yarn such as the yarn core or hairiness.

Speed encoder 26 is preferably used to measure the lengths of yarn transported by drive mechanism 24. The output of encoder 26 is then translated into yarn lengths and yarn speed by computer 22. Keyboard 28 is used by the operator to enter commands for operation for computer 22 in a known fashion. The output of the device may then be applied to either CRT 30 and/or printer 32 as desired.

Figure 2:
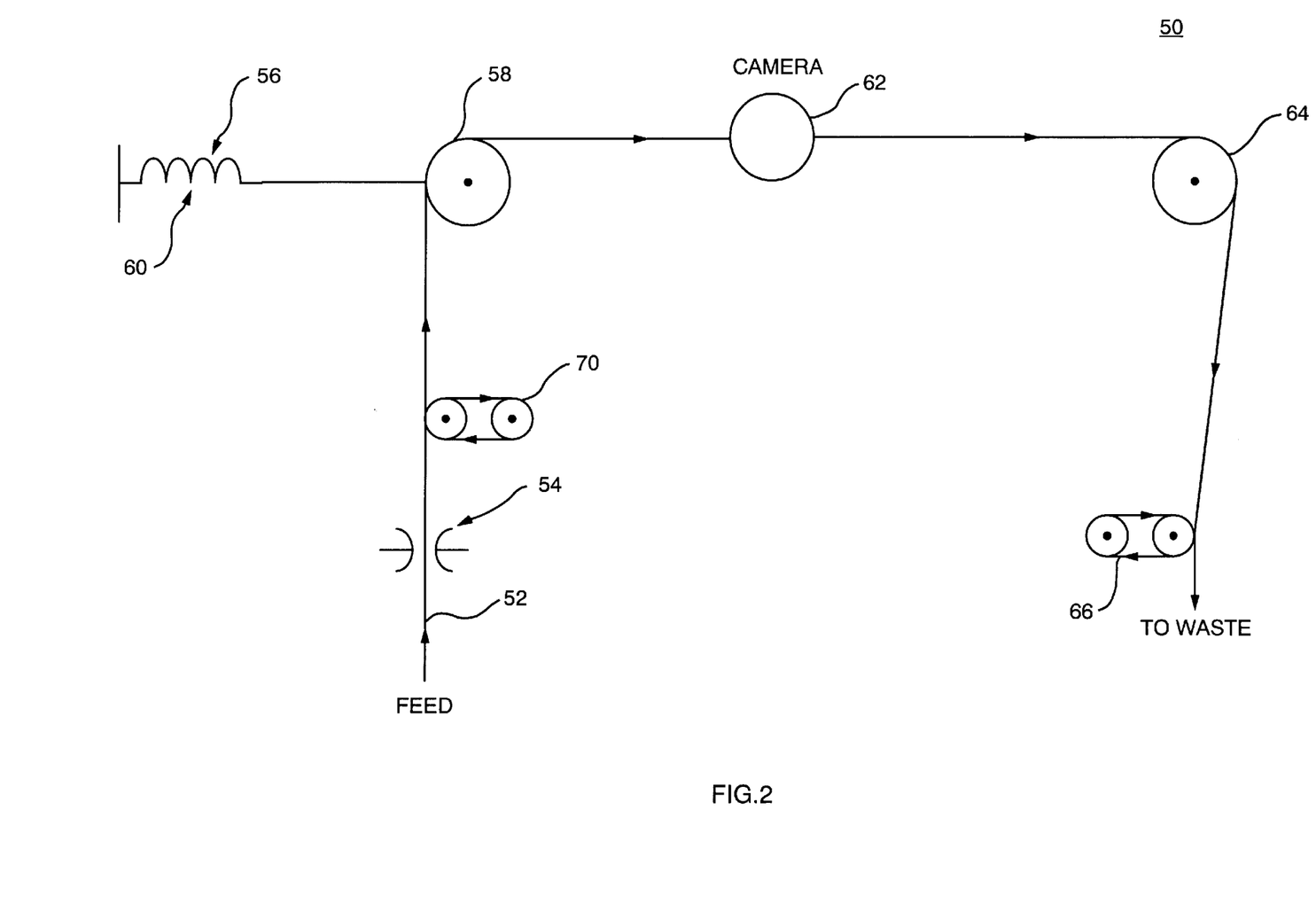
FIG. 2 is a highly schematic view of a preferred embodiment of the device of FIG. 1.

Preferred embodiment 50 of the yarn measurement and imaging for the yarn diameter measurement and fabric simulation system useful in this invention is shown schematically in FIG. 2. Yarn 52 is passed through pretension device 54, around a first set of feed rolls 70, and then through constant tension device 56 schematically depicted as roller 58 and adjustable tension spring 60. Device 56 preferably allows the operator to select the tension applied to yarn 52 from ½ to 750 grams. Camera 62 images the yarn and provides the image to the computer. In a preferred embodiment, the linear CCD array described above is employed and operated at about 3,200 scans per second with the yarn diameters measured and stored for selected lengths of yarn with the yarn running at selected speeds. This is accomplished with a clock running at approximately 15 MHz. The yarn is then directed by roller 64 to driven roll pairs 66 around which yarn 52 is wound one or more times to pull the yarn through camera 62.

Figure 3:
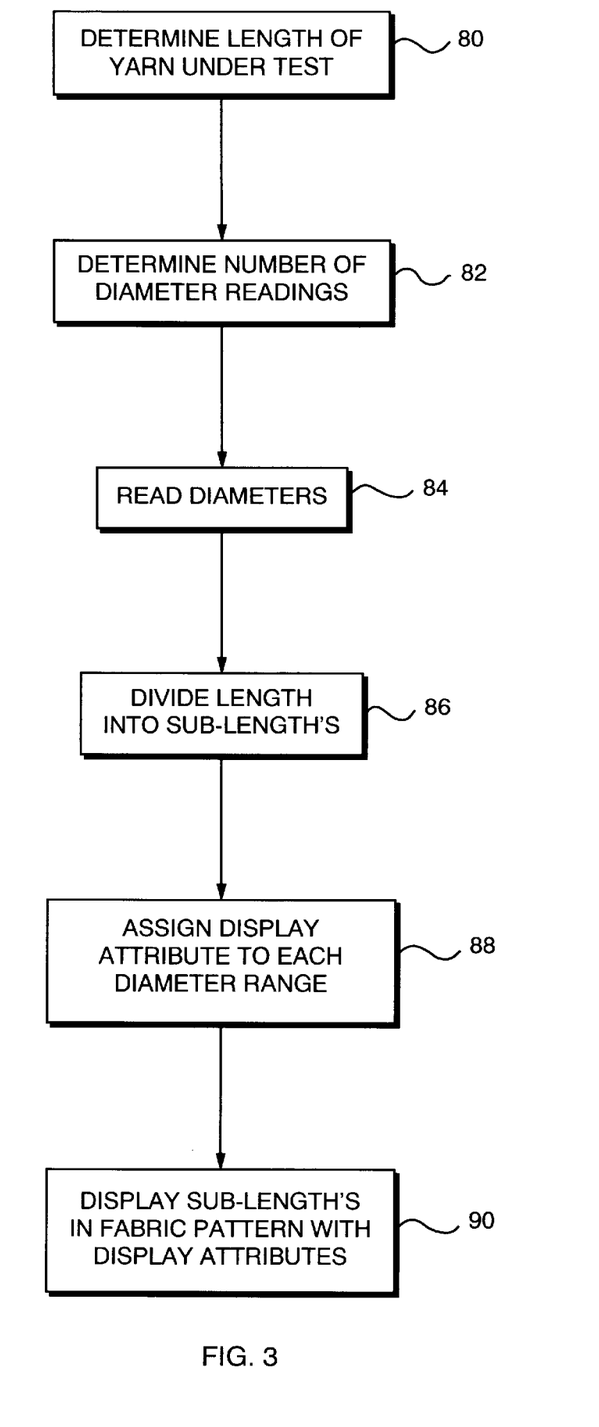
FIG. 3 is a flow chart of the operation of the device of FIG. 1 according to a preferred embodiment of this invention.

A flow chart for operation of a preferred embodiment of the system of this invention, using the equipment shown in FIGS. 1 and 2, is shown in FIG. 3. The system first determines the length of yarn to be tested, preferably under operator control. Then the system determines the number of diameter readings to take for that length. The maximum number would be set either by the amount of available memory or the yarn speed and length under test versus the measurement device clock speed, which would determine the number of measurements taken per unit length.

The system reads the diameters, step 84, by moving the yarn through the imaging area as shown in FIGS. 1 and 2. In a preferred embodiment, the diameter is calculated based on the two farthest-spaced pixels of the CCD array which are considered to be blocked by the yarn, regardless of any intervening unblocked pixels, so that, for example, hairiness projecting from the yarn core is measured as contributing to the overall diameter of the yarn. By adjusting the amount of received light which is considered to represent a blocked pixel, the operator may in effect filter out or emphasize such hairiness or other less dense yarn areas as desired.

The system then divides the measured length of yarn into a number of sub-lengths for analysis, storage and/or display, step 86. The system then assigns display attributes or parameters to each diameter or diameter range, step 88. This may be accomplished as described above for a grey scale image. Alternatively, fewer shades of grey, or colors, may be used. In any case, each diameter or each diameter range as established by the operator is assigned a different display attribute, or representation parameter, such as a quantitative value, color or shade of grey. Every one, or some of, the sub-lengths are then either stored into memory for display with another yarn sample to be measured subsequently, or displayed immediately in a fabric pattern, with those display parameters, step 90, to accomplish an electronic version of the standard fabric sample used for determining the general regularity of the fabric as set forth in the ASTM standard, or for display and/or analysis in a rectangular or taper-board pattern.

The disclosure of commonly-assigned U.S. Pat. No. 5,319,578, and copending applications Ser. No. 08/252,346, filed Jun. 1, 1994, and Ser. No. 08/209,421, filed Mar. 10, 1994, are incorporated herein by reference.

In one embodiment of a fabric pattern quality determination, the measurements of one yarn sample would be used to represent the weft yarn of the fabric and the measurements of a number of other yarn samples would be used to represent the warp yarns. This mimics actual woven fabric construction wherein a singular weft yarn is passed back and forth perpendicular to and interlaced with a multitude of parallel warp yarns.

The system could also be enabled to store and display, next to the image of the simulated fabric, images of standard fabric in a similar manner to the standard fabric image photograph used in the ASTM standard. This would allow the operator in a single screen to compare the electronically-imaged fabric to standard fabrics to determine the fabric grade. Appearance and color consistency can be compared in this manner.

Figure 4:
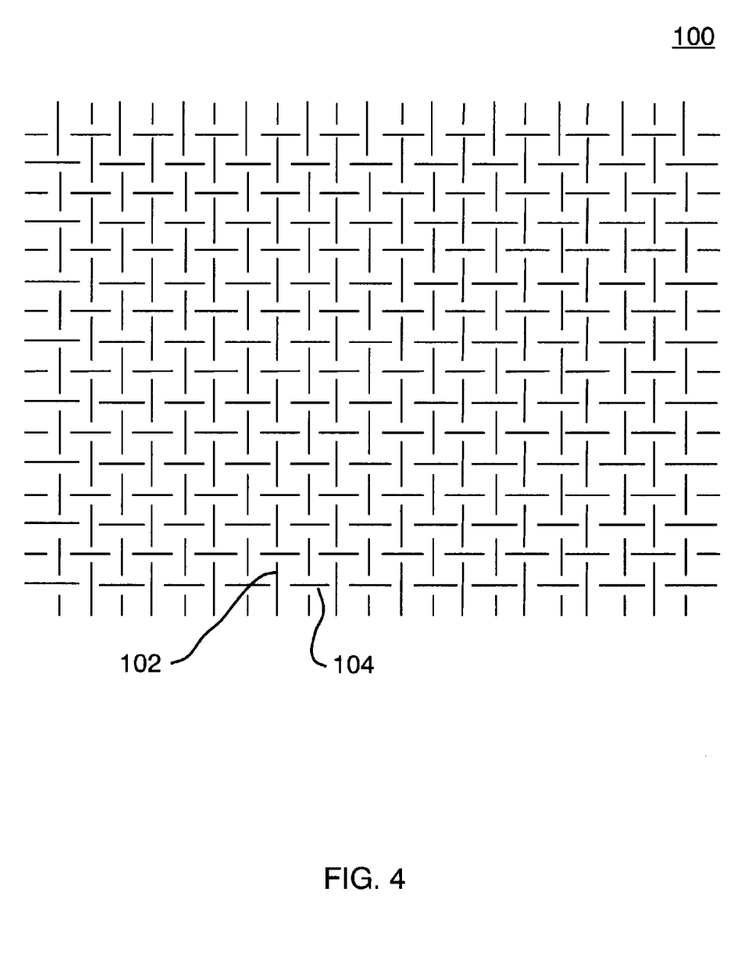
FIG. 4 is an illustration of a typical weave pattern for use within the invention.

A standard 1/1 or Plain weave fabric pattern 100 is depicted in FIG. 4 without yarn variations. Weft yarn 102 is positioned vertically. Warp yarns 104 are positioned horizontally.

Figure 5:
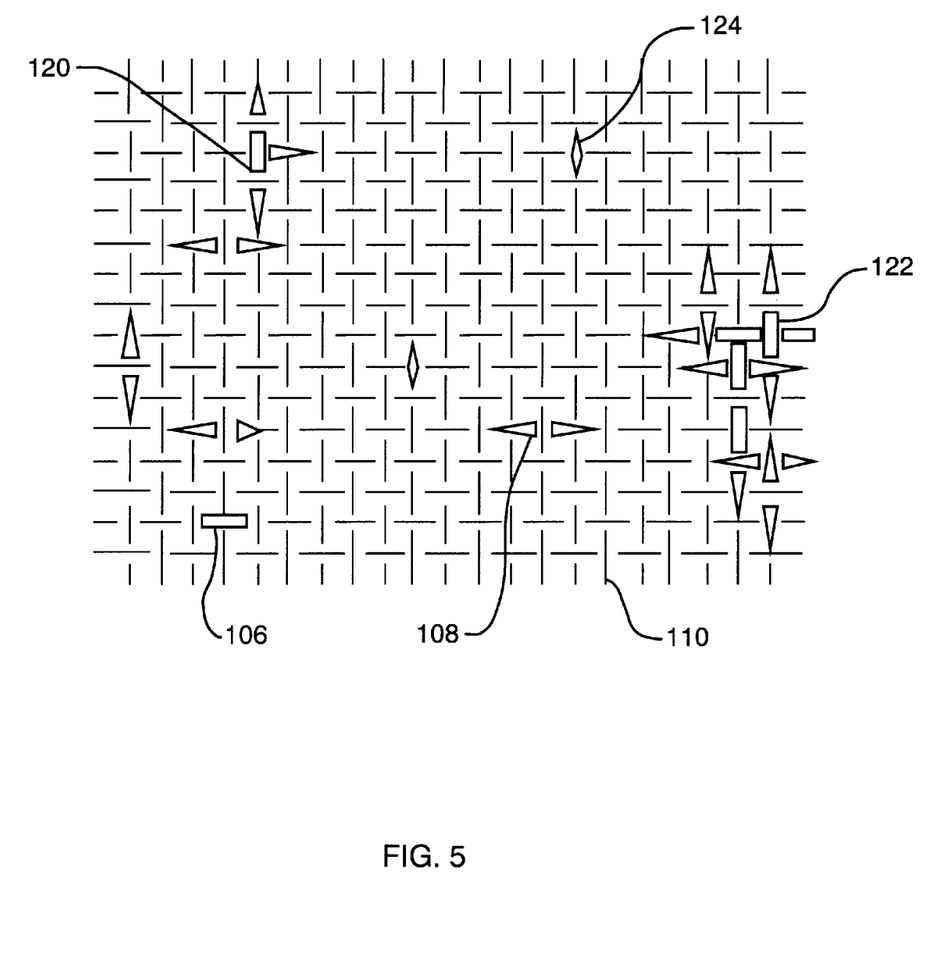
FIG. 5 is a typical display of a simulated weave according to a preferred embodiment of this invention.

In FIG. 5 the same pattern as in FIG. 4 is depicted but including yarn diameter variations such as area 106. In this example, other yarn variations are ignored and only yarn portions having excessively large diameters are represented, such representations being accomplished by wider than normal black lines 108 at the locations of the wide yarn diameters, all other portions of the yarn are represented by thinner uniform black lines 110. Alternatively, one or more types of measured events could be displayed. In such a fabric sample as herein depicted, a skilled examiner may instantly recognize several events. In the first event 120, a series of three variations are found. In the second event 122, a grouping of seven variations are found. Other variations 124 scattered randomly about the patch may or may not qualify as events, depending on the yarn qualities being considered. At any rate, at least one of the qualities of a fabric which may be woven into a plain weave from such yarns can be examined herein without the effort and expense of actual weaving.

Because the yarn diameter variations have been quantitatively measured, the events may be further quantified by many known analytical methods to provide precise values to each event which may then be compared to a predetermined threshold. Such may determine that certain events are acceptable and certain others are not. In the display 130 depicted in FIG. 6, the weave of FIG. 5 has been more quantitatively displayed. The area within adjacent warp 132 and weft 134 yarns defines a cell 136. The number of excessively wide warp and weft yarns, which were depicted as wide black lines in FIG. 5, surrounding each cell have been counted. All cells having one, two, three and/or four excessively wide warp or weft lines therearound may be fully blackened as shown at cell 138. The number of blackened cells may be counted as events, or the distribution of blackened cells may be further analyzed to provide a mathematical method of quantifying fabric quality. Alternatively, individual pixels could be counted, for instance those having a certain color or grey scale value.

Figure 6:
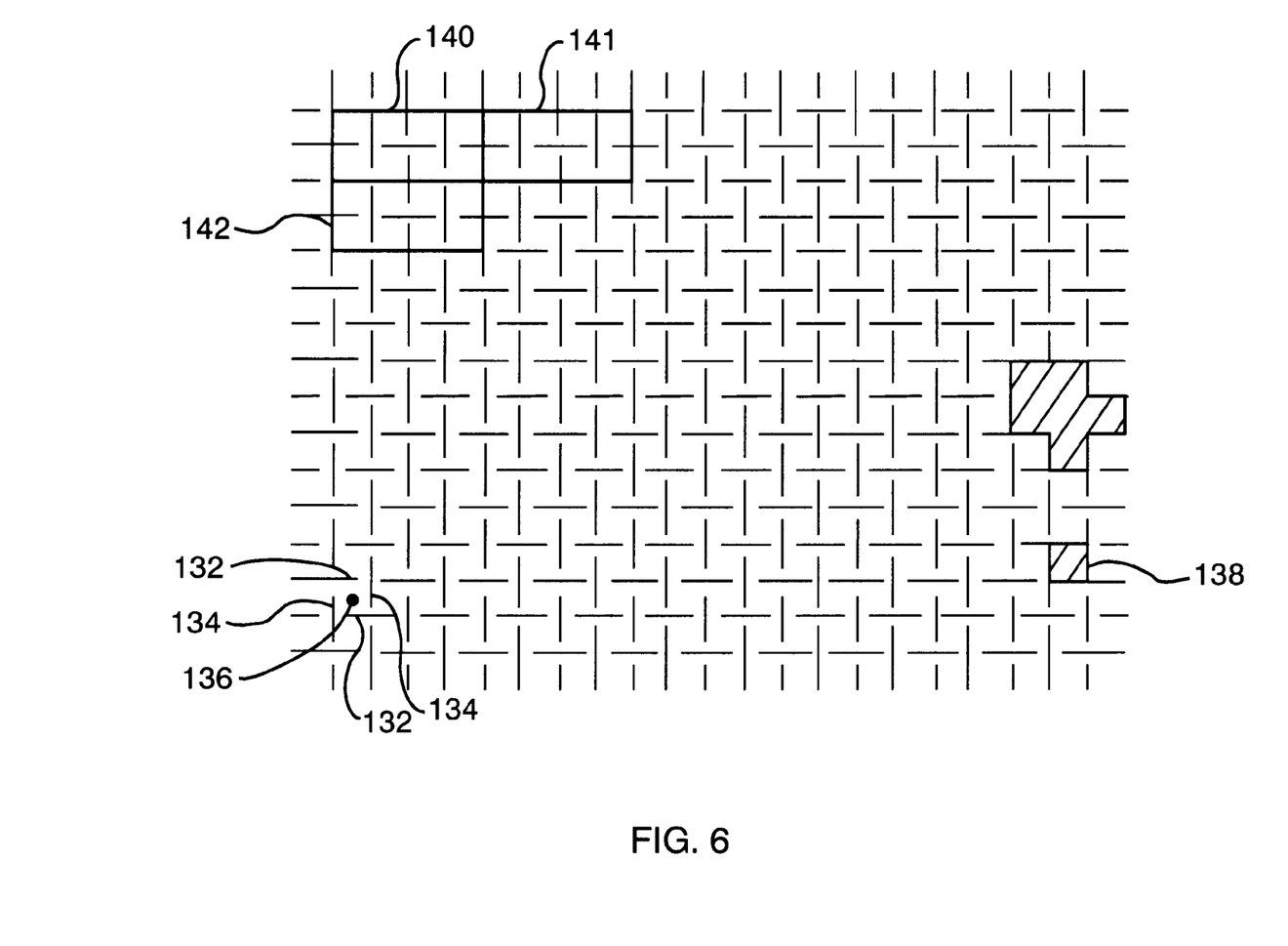
FIG. 6 is another example of a display according to a preferred embodiment of this invention.

Also depicted in FIG. 6 are examples of display cells that can be used to determine patterns of events, for both grading purposes as well as for use in dynamic yarn clearing in order to upgrade the quality of the yarn, or a fabric to be produced from the yarn. Cells 140 and 141 are horizontally adjacent, while cell 142 is vertically adjacent to cell 140. Each depicted cell encompasses a given length of either or both of the weft and warp yarns. Cells could also be used to evaluate the yarn itself, before any simulated weaving or knitting-this would allow automation of the manual taper or rectangular board inspection currently practiced.

Figure 7:
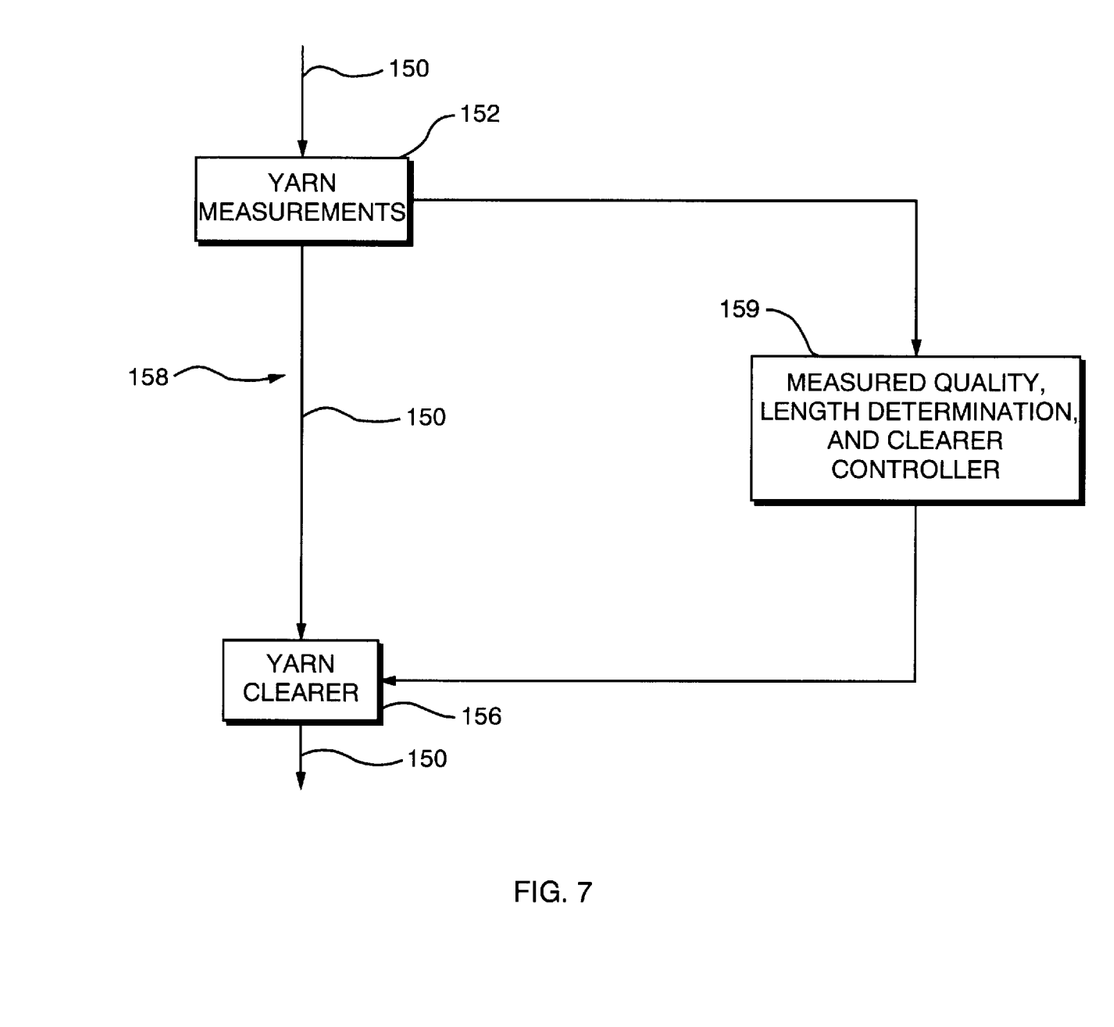
FIG. 7 is a schematic diagram of dynamic yarn clearing according to this invention.

The dynamic yarn clearing of this invention is schematically depicted in FIG. 7. The necessary measurement(s) are made on yarn 150 by measurement device(s) located at 152. Measurement data is provided to measured yarn quality and measured length determinator 154, which determines the amount of yarn measured, and the measured qualities, to determine events. Block 154 would be accomplished with the computer. It would, in response to these measurements and their analysis in any of the manners described above, instruct the yarn clearer 156 to cut portions from the yarn to achieve the desired result. For example, one or more events occurring in one or more cells could be removed in order to do away with a pattern of events that affected the grade for example the types of patterns that are schematically depicted in FIGS. 5 and 6. Reservoir 158 of yarn 150, between measurements 152 and clearer 156, is provided having a sufficient length of yarn so that at the running speed there is sufficient length to allow time to make the necessary clearing decisions. The reservoir also provides a base yarn length that is used to create a measured "batch" for dynamic, continuous determination and upgrade of the yarn on a "batch-by-batch" basis as it runs through the system.

Clearing decisions are based on the measurement and analysis of one or more yarn qualities, and of the length of the measured yarn. Current clearing technology makes clearing decisions mechanically, based only on a single measured yarn quality, such as thick or thin spots, and not at all based on the length of measured yarn. Also, clearing is accomplished today on yarn without any thought as to the fabric that is to be produced using the yarn. The dynamic clearing of this invention can make clearing decisions based on the appearance of the fabric to be produced from the yarn, which ultimately is all that matters in yarn production. Accordingly, current clearing technology removes more yarn than necessary, which slows and increases the expense of yarn production.

Figure 8A:
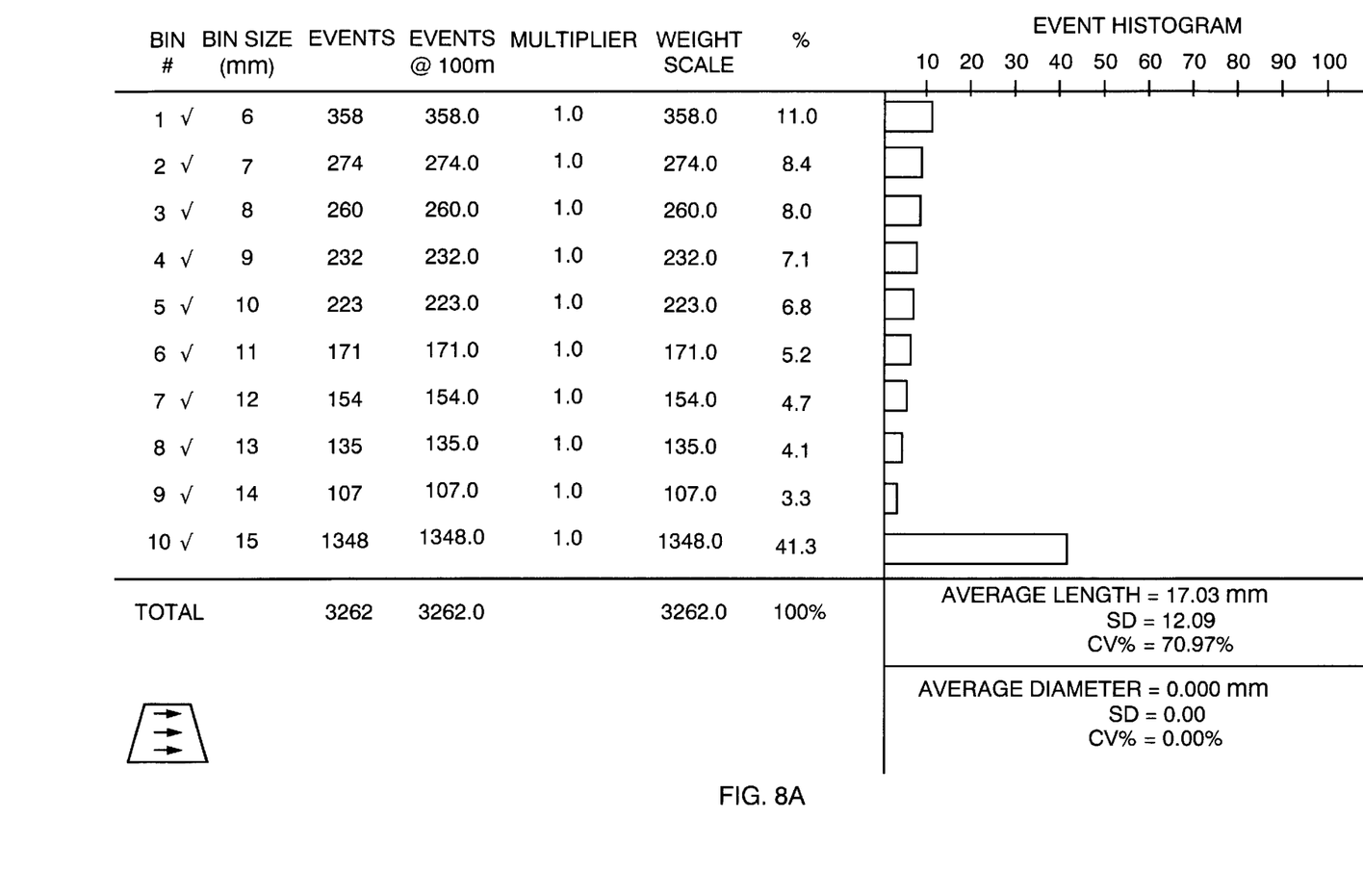
FIGS. 8A and 8B when viewed together are a printer output displaying a yarn with an unacceptable moiré pattern.
Figure 8B:
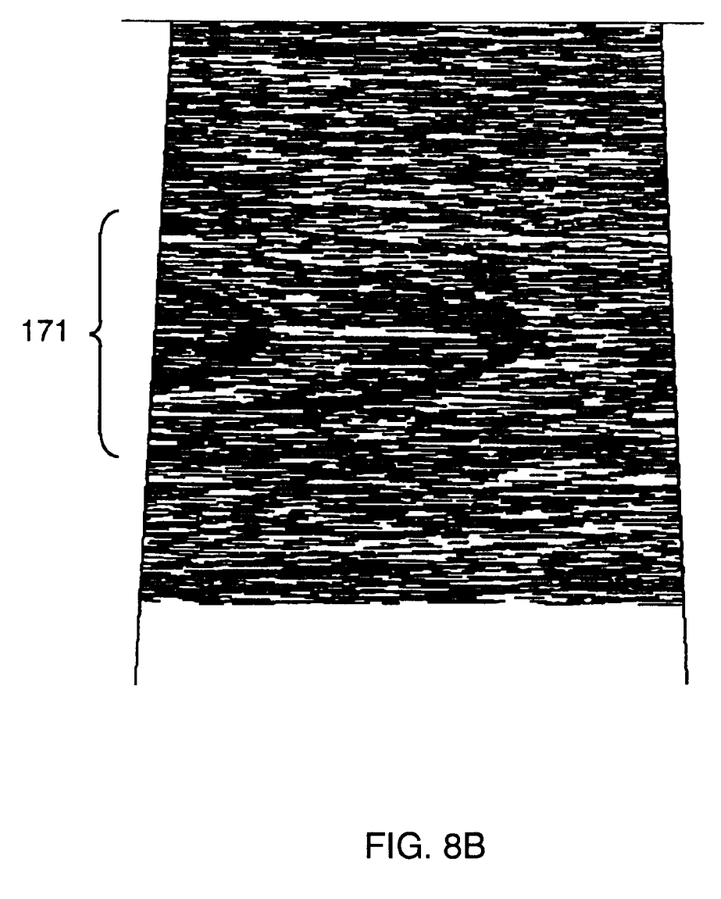

FIGS. 8A and 8B detail a printer output of measured yarn with the yarn representations laid side-by-side to mimic the traditional taper board test. The yarn was measured with the apparatus detailed above. 100 meters of the yarn were measured in one minute. Diameter measurements were taken at 19.4 locations per centimeter. The diameter and data was interpreted based on the lengths of areas of the yarn having a diameter of over the 0.26 mm threshold. The reported "bins" 1 through 10 are, as shown, the reported number of locations (called "events") along the measured length of yarn in which the diameter was at least as great as the threshold continuously for the stated length. In other words, bin one included events with a length of at least 6 and less than 7 millimeters. 358 such events were measured in the 100 meters of yarn.

Each measured event is represented in the taper board display with a line segment having a length directly related to the event length, in which the width of the line segment is constant. As can be seen, there is a moiré pattern of events that repeat at a periodicity which is related to the width of the display in area 171. Any loom using such width would produce a fabric with this type of defect.

Figure 9A:
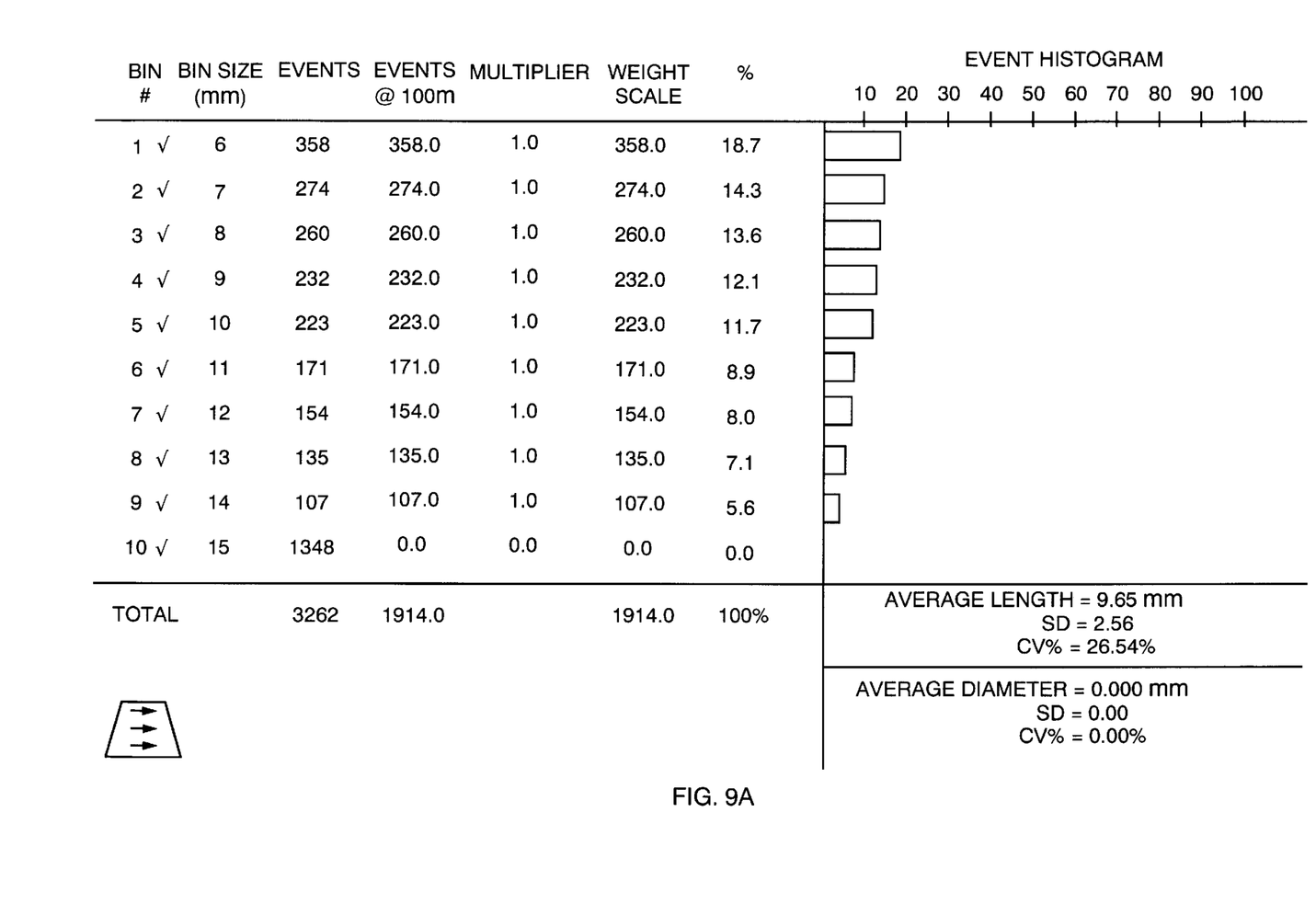
FIGS. 9A and 9B when viewed together are the same display with all of one type of event electronically deleted, illustrating the improved fabric quality without the moiré pattern.
Figure 9B:
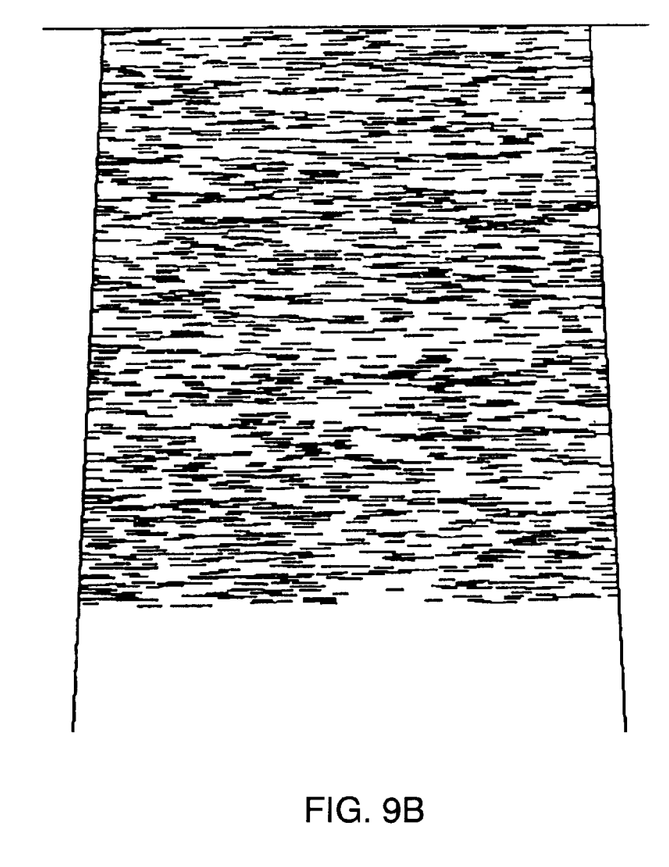

FIGS. 9A and 9B are an identical output with the exception that bin 10 has been deleted from the output. No moiré pattern is visible, indicating that the moiré pattern is established by the 15 millimeter long events. Accordingly, to upgrade the measured yarn for use in a loom which would have produced the moiré pattern, it would be necessary to delete all (or perhaps some of) the 15 millimeter long events. The yarn clearer detailed above could be automatically enabled to do so to create a yarn of a higher grade.

Some of the system variables that may be established by the operator for the system of this invention include the fabric weave pattern, simulated fabric sample size, measured yarn samples from which the weft and warp yarns are selected, yarn qualities to be included in the display, the display and the display attribute for each of those qualities or of their assigned values, and event threshold levels.

This invention can be utilized to grade yarns and electronically produced "fabrics", for dynamic yarn clearing, and to evaluate color, entanglements, hairiness, friction, twist, and air texturing, in addition to other discussed purposes.

Multiple measured yarn qualities could be selected to allow the operator to grade the fabric, and automatically counted and tabulated by the system. The system may be programmed to evaluate fabric quality electronically by quantifying yarn variations and their relationships in the simulated fabric. The system may be programmed to count events or to recognize groupings of certain grey or color scale values as they occur in a given screen display and to produce quantitative measurements of fabric appearance.

The computer of this invention can be programmed to include a neural network of the type currently known in the field of artificial intelligence. The neural network would be used to automatically grade measured yarns, and/or fabrics electronically produced by this invention. The neural network would be "taught" with input garnered from expert human graders who follow the standard tests. These inputs would be used in the neural network to establish proper weighting and combinations of measured events to establish grades as a human would. The neural network would also be input with grading rules. The cells could be used in such a system to recognize patterns of events that affect the grade.

Figure 10:
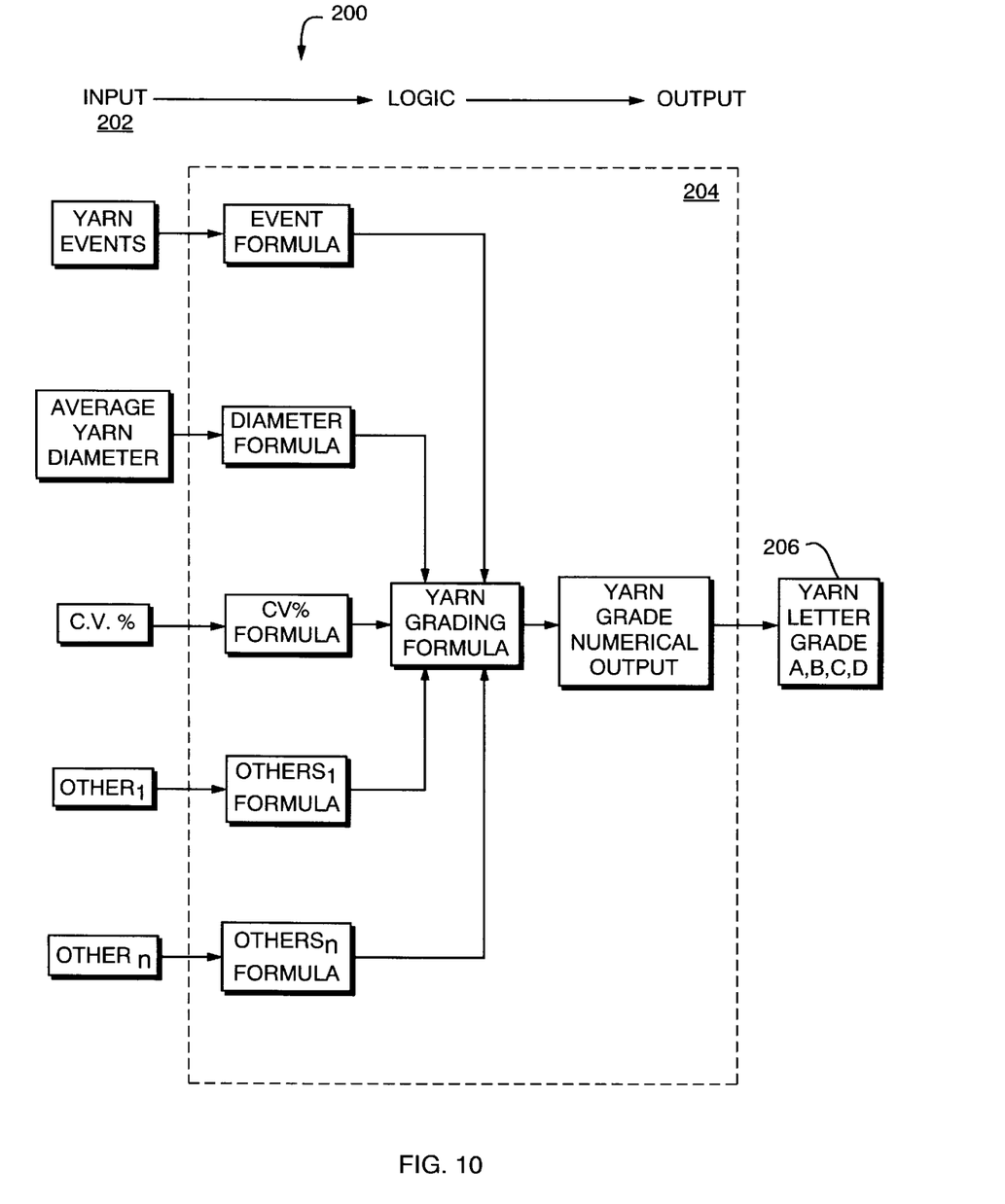
FIG. 10 is a block diagram of a neural network useful in this invention.

An example of such use of a neural network to determine overall yarn quality based on a number of measured yarn qualities is schematically depicted in FIG. 10. Using the system detailed in FIGS. 1 and 2, the yarn diameter at a large number of closely spaced locations along a length of a running yarn are measured. The results of such measurement are shown in FIGS. 8A, 8B, 9A and 9B and described above. From this data the average yarn diameter and the coefficient of variation of the yarn diameter may be determined. This information is input into neural network logic 204 to determine a letter grade of the measured yarn. Input column 202 also includes potential inputs for other data 1 to n, indicating that the grading can be based on additional yarn quality measurements as described above. One important example would be color, since color variation obviously has a drastic effect on the appearance on fabric made from the measured yarn.

Thus, the neural network is effectively a more advanced yarn grading system than one based only on measured yarn event information. The neural network logic includes formulae for interpreting each input, and a yarn grading formula which would properly weight the results of the formulae. From this would be derived a numerical output which would result from the neural network's evaluation and weighting and combination of the input data. Output 206 could be a yarn letter grade, for example grade "A", to follow the standard ASTM grading representation. This would be accomplished by assigning letter grades to certain yarn grade numerical output ranges.

Therefore, although specific features of the invention are shown in some drawings and not others, this is for convenience only as some features may be combined with any or all other features in accordance with the invention.

Other embodiments will occur to those skilled in the art and are within the following claims:

What is claimed is:

1. A method of dynamically clearing yarn, comprising:

measuring one or more qualities of a running yarn and locating positions on said running yarn where measured qualities exist, wherein each located position comprises an instance of any one of said one or more qualities;

measuring the length of the running yarn on which said one or more qualities are measured;

counting instances of said one or more qualities within the measured length of the running yarn;

providing a yarn clearer downstream of, and in the path of, the running yarn; and cutting out portions of the measured length of running yarn by automatically commanding said yarn clearer based on both said measured length of running yarn and the number of instances of said one or more measured qualities within said measured length of running yarn.

2. A method for measuring and locating selected fiber qualities and dynamically clearing fibers on-line, comprising:

measuring a running fiber sample to determine the location and magnitude of selected fiber qualities;

converting said measurements into one or more corresponding representations thereof, wherein the location and magnitude of each fiber quality comprises an event, and wherein said representation includes said events at each event's corresponding location along the length of each said fiber sample;

superimposing said one or more representations onto a predefined arrangement to simulate the interlacing thereof and thereby facilitate the evaluation of the qualities of fibers as they would predictably be affected by the fiber qualities;

providing a yarn clearer downstream of, and in the path of, the running fiber; and cutting out portions of the measured length of running yarn by commanding said yarn clearer based on one or more selected fiber qualities.

* * * * *